US00PP22222P2

(12) United States Plant Patent
Staalduinen

(10) Patent No.: US PP22,222 P2
(45) Date of Patent: Nov. 1, 2011

(54) ***EUPHORBIA* PLANT NAMED 'GL HIP HOP'**

(50) Latin Name: *Euphorbia hypericifolia*
Varietal Denomination: GL Hip Hop

(75) Inventor: Eelco van Staalduinen, 's-Gravenzande (NL)

(73) Assignee: Keep Smiling B.V., 'S-Gravenzande (NL)

( * ) Notice: Subject to any disclaimer, the term of this patent is extended or adjusted under 35 U.S.C. 154(b) by 0 days.

(21) Appl. No.: 12/799,768

(22) Filed: Apr. 30, 2010

(51) Int. Cl.
*A01H 5/00* (2006.01)

(52) U.S. Cl. ..... Plt./302

(58) Field of Classification Search ..... Plt./302
See application file for complete search history.

*Primary Examiner* — Susan McCormick Ewoldt
(74) *Attorney, Agent, or Firm* — Mark P. Bourgeois

(57) ABSTRACT

A new and distinct *Euphorbia* plant cultivar is disclosed, characterized by a compact, upright, slightly outwardly spreading plant habit; free branching and free flowering habit; small, dark green foliage; and small, pure white flower bracts.

1 Drawing Sheet

Latin name of the genus and species: *Euphorbia hypericifolia.*

Variety denomination: 'GL HIP HOP'.

BACKGROUND OF THE INVENTION

The new cultivar 'GL Hip Hop' is a product of a selection of seed from *Euphorbia chamaesyce*, (not patented). The exact parent plants are unknown. The new cultivar was discovered and selected as a single plant by Eelco van Staalduinen in a controlled environment in Worms, Germany in May of 2007.

Asexual reproduction of the new cultivar 'GL Hip Hop' by terminal cuttings was performed in Oxnard, Calif., and has shown that the unique features of this new cultivar are stable and reproduced true to type on successive generations.

SUMMARY OF THE INVENTION

The cultivar 'GL Hip Hop' has not been observed under all possible environmental conditions. The phenotype may vary somewhat with variations in environment such as temperature, daylength, and light intensity, without, however, any variance in genotype.

The following traits have been repeatedly observed and are determined to be the unique characteristics of 'GL Hip Hop.' These characteristics in combination distinguish 'GL Hip Hop' as a new and distinct *Euphorbia* cultivar:

1. Compact, upright, slightly outwardly spreading plant habit;
2. Free branching and free flowering habit;
3. Small, dark green foliage; and
4. Small, pure white flower bracts.

In comparison to the commercially available variety 'Inneuphdia' (U.S. Plant Pat. No. 17,567), 'GL Hip Hop' is taller and wider than the comparable variety. In addition, 'GL Hip Hop' has darker green foliage. Also, 'GL Hip Hop' has smaller leaves and smaller flowers. Finally, the flowers bracts are a more pure white color than the comparable variety.

BRIEF DESCRIPTION OF THE PHOTOGRAPH

The accompanying photograph illustrates in full color a typical plant of 'GL Hip Hop' grown in a 1 gallon container.

One cutting was used in the pot, planted mid May and grown under outdoor field conditions. The colors are as nearly true as is reasonably possible in a color representation of this type.

DETAILED BOTANICAL DESCRIPTION

In the following description, color references are made to The Royal Horticultural Society Colour Chart except where general terms of ordinary dictionary significance are used. The following observations and measurements describe 'GL Hip Hop' plants grown in Oxnard, Ventura County, Calif., during the months of May through October 2006. The growing temperature ranged from 12° C. to 15° C. at night to 12° C. to 20° C. during the day. Measurements and numerical values represent averages of typical flowering types.

Botanical classification: *Euphorbia hypericifolia* cultivar 'GL Hip Hop.'

Commercial classification: *Euphorbia.*

PROPAGATION

Type: By cuttings.
Time to initiate roots, summer: About 12 days at 22° C.
Time to initiate roots, winter: About 14 days at 22° C.
Time to develop roots, summer: About 16 days at 22° C.
Time to develop roots, winter: About 18 days at 22° C.
Root description: Fine, white in color.
Rooting habit: Freely branching.

PLANT

Growth habit: Compact and mounded plant habit; plants upright and slightly outwardly spreading.
Height: Approximately 36.8 cm.
Plant spread: Approximately 48.3 cm.
Growth rate: Slow.
Branching characteristics: Free Branching with four primary branches with secondary and tertiary lateral branches on each plant.
Lateral branch characteristics:
*Length.*—Approximately 30.5 cm.
*Diameter.*—Approximately 2 mm.

*Internode length.*—About 3.5 cm.
*Strength.*—Moderate.
*Texture.*—Smooth.
*Color.*—Near Green 138A.

FOLIAGE

Leaf:
*Arrangement.*—Opposite, simple.
*Average length.*—Approximately 2.4 cm.
*Average width.*—Approximately 0.8 cm.
*Shape of blade.*—Ovate.
*Apex.*—Acuminate.
*Base.*—Rounded.
*Attachment.*—Stalked.
*Margin.*—Entire.
*Texture of top surface.*—Lightly pubescent.
*Texture of bottom surface.*—Lightly pubescent.
*Color.*—Young foliage upper side: Near Green 137A. Young foliage under side: Near Green 138B. Mature foliage upper side: Near Green 137A. Mature foliage under side: Near Green 138A.
*Venation.*—Type: Pinnate. Venation color upper side: Near Yellow-Green 146B. Venation color under side: Near Yellow-Green 146B.

Petiole:
*Average length.*—Approximately 1 cm.
*Color.*—Near Green 137A.
*Diameter.*—Less than 1 mm.

INFLORESCENCE

Inflorescence description:
*Natural flowering season.*—Spring to summer.
*Flowering habit.*—Continuous, self-cleaning.
*Flower arrangement.*—Single rotate flowers arranged in umbel-like compound terminal cymes. Freely flowering with about 600 flower buds and flowers per plant, facing upright and outwardly.
*Persistence.*—Persistent.
*Fragrance.*—None detected.
*Inflorescence height.*—About 1.2 cm.
*Inflorescence diameter.*—About 1.3 cm.
*Flower diameter.*—About 6 mm.
*Flower depth.*—About 7 mm.
*Longevity.*—About 12 days.

Floral bracts:
*Quantity.*—Two.
*Arrangement.*—Opposite.
*Length.*—About 6 mm.
*Width.*—About 2 mm.
*Shape.*—Elliptical.
*Apex.*—Rounded.
*Base.*—Fused.
*Margin.*—Entire.
*Texture, upper and lower surfaces.*—Smooth.
*Color.*—When opening and fully expanded: Upper surface: Near White 155B. Lower surface: Near White 155B.
*Peduncles.*—Length: About 5 cm. Diameter: About 1 mm. Strength: Moderate. Angle: About 60 to 90 degrees from vertical. Texture: Smooth. Color: Near Green 138A.
*Pedicels.*—Length: About 3 mm. Diameter: Less than 1 mm. Strength: Moderate. Angle: About 45 degrees from vertical. Texture: Smooth. Color: Near Green 138A.
*Cyathia.*—Length: About 6 mm. Diameter: About 3 mm. Shape: Oval; eight terminal points. Aspect: Upright. Color: Near Green 146A.
*Nectaries.*—Quantity: About three or four per flower. Shape: Lunate. Length: About 2 mm. Width: About 2 mm. Color: Near Green 147A.

REPRODUCTIVE ORGANS

*Androecium.*—Quantity: About four stamens per cyathia. Shape: Oval, bi-lobed. Length: Less than 1 mm. Color: Near White 158D. Pollen: Scarce. Pollen color: Near 158D.
*Gynoecium.*—Quantity: One per cyathia. Pistil length: About 2 mm. Style length: Less than 1 mm. Style color: Near White 155B. Stigma shape: Six-parted. Stigma color: Near White 155D. Ovary color: Near Yellow-Green 146A.

OTHER CHARACTERISTICS

Disease resistance: Neither resistance nor susceptibility to diseases or pests has been observed in this variety.
Drought tolerance/cold tolerance: Plants of the new cultivar are tolerant to temperatures as low as 10° C. and as high as 40° C.
Fruit/seed production: Commercially, this plant is not used or observed in a stage where fruit or seeds would be produced. Therefore, seed or fruit production has not been observed.

What is claimed is:

1. A new and distinct cultivar of *Euphorbia* plant named 'GL Hip Hop' as herein illustrated and described.

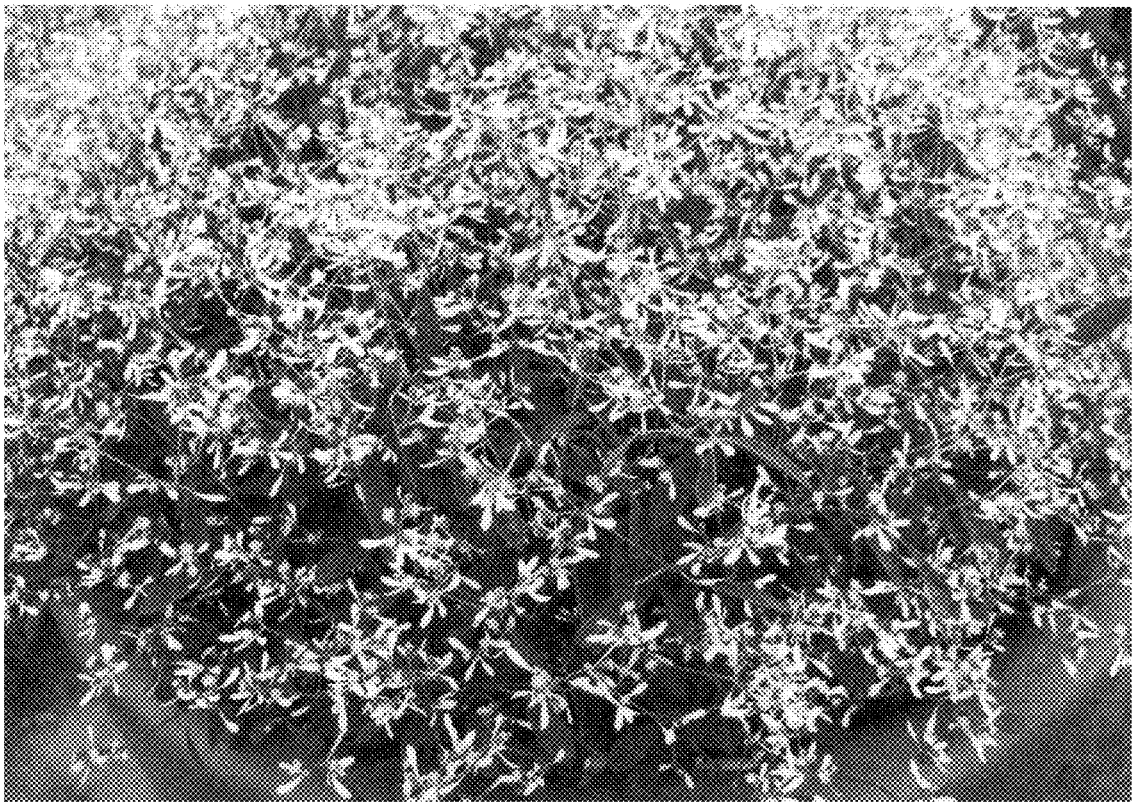

* * * * *